United States Patent
Chi et al.

(10) Patent No.: US 7,002,013 B1
(45) Date of Patent: Feb. 21, 2006

(54) PT COMPLEXES AS PHOSPHORESCENT EMITTERS IN THE FABRICATION OF ORGANIC LIGHT EMITTING DIODES

(75) Inventors: Yun Chi, Hsinchu (TW); Pi-Tai Chou, Taipei (TW); Sheng-Yuan Chang, Hsinchu (TW); Jakka Kavitha, Hsinchu (TW); Yu-Tai Tao, Taipei (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 10/947,162

(22) Filed: Sep. 23, 2004

(51) Int. Cl.
*C07D 401/14* (2006.01)
*C07D 403/14* (2006.01)

(52) U.S. Cl. ............... 546/10; 544/225; 546/2; 546/8; 502/167

(58) Field of Classification Search ........... 546/10, 546/8, 2; 544/225; 502/167
See application file for complete search history.

(56) References Cited

FOREIGN PATENT DOCUMENTS

WO    WO 00/43405    *  7/2000

* cited by examiner

*Primary Examiner*—Charanjit S. Aulakh
(74) *Attorney, Agent, or Firm*—Bacon & Thomas, PLLC (57) ABSTRACT

A series of Pt(II) complexes having the following formula are disclosed:

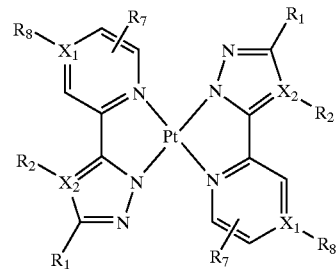

$X_1$ and $X_2$ independently are C or N, $X_1$ can also locate at another position of the hexagonal ring, when $X_1$ is N;

$R_1$ is H, C1–C8 alkyl, or C1–C4 perfluoroalkyl, $R_2$ is H, $R_1$ and $R_2$ together are C4–C8 alkylene, or $R_1$ and $R_2$ together are bridged carbocyclic C4–C12 alkylene, when $X_2$ is C;

$R_1$ is H, C1–C8 alkyl, or C1–C4 perfluoroalkyl, and $R_2$ is omitted, when $X_2$ is N;

$R_7$ is H or methyl, and $R_8$ is omitted, when $X_1$ is N;

$R_7$ is H or methyl, $R_8$ is H or methyl, or $R_7$ and $R_8$ together are

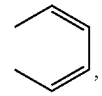

, when $X_1$ is C.

26 Claims, 6 Drawing Sheets

PT COMPLEXES AS PHOSPHORESCENT EMITTERS IN THE FABRICATION OF ORGANIC LIGHT EMITTING DIODES

FIELD OF THE INVENTION

The present invention relates to an organic light emitting diode (OLED), particularly an OLED containing a Pt(II) complex as a phosphorescent emitter.

BACKGROUND OF THE INVENTION

Owing to their potential to harness the energies of both the singlet and triplet excitons after charge recombination, transition metal based phosphorescent materials have recently received considerable attention in fabricating organic light-emitting diodes (OLEDs). The main advantages are due to the heavy atom induced singlet-to-triplet intersystem crossing as well as the large enhancement of radiative decay rate from the resulting triplet manifolds. In this regard, numerous attempts have been made to exploit third-row transition metal complexes as dopant emitters for OLED fabrication, among which quite a few Pt(II), Os(II) and Ir(III) complexes have been reported to exhibit highly efficient device performances. Despite these developments, attempts to further expand the potential of the square planar Pt(II) complexes, in which the central metal ion possesses a higher atomic number than Os(II) and Ir(III) for efficient OLED applications, has encountered many intrinsic obstacles. For example, the PtOEP ($H_2OEP$=octaethylporphyrin) type of emitter commonly has a ligand based phosphorescence with lifetimes as long as 30~50 $\mu s$, so that saturation of emissive sites and a rapid drop in device efficiency at high drive current is observed. Also contributing to the poor device efficiency is the planar molecular configuration of many Pt(II) complexes, which leads to a stacking effect and hence the formation of aggregates or dimers that tend to form excimers in the electronically excited state. To recognize the potential of Pt(II) materials for applications in high efficiency OLEDs, the rational design of Pt(II) complexes aimed at reduction of the phosphorescence radiative lifetime and the prevention of stacking behaviour is critical.

SUMMARY OF THE INVENTION

In this invention, we disclose the design and synthesis of a new series of emissive Pt(II) complexes, in which the associated ligand chromophores possess a bulky, rigid architecture to effectively suppress the aggregation effect. Moreover, drastic reduction of the phosphorescence radiative lifetime to several microseconds has also been achieved due to the strong singlet-triplet state mixings. In one of the preferred embodiments of the present invention, highly efficient Pt(II) OLEDs operating at 610~630 nm have been successfully prepared for the first time, in which the dopant (Pt(II) complexes) concentrations, due to the diminution of aggregation effect, can be substantially increased to maximize the performance.

A primary objective of the present invention is to provide a phosphorescent Pt complex for use as a light emitter in the fabrication of an organic electroluminescent device.

Another objective of the present invention is to provide a series of Pt complexes for use as a light emitter in an electroluminescent device capable of emitting green, orange and red light.

The preferred embodiments of the phosphorescent Pt complex synthesized according to the present invention include (but not limited to):

1. The phosphorescent Pt complex possessing the following generalized structure:

wherein $X_1$ and $X_2$ independently are C or N;

$R_1$ is H, C1–C8 alkyl, or C1–C4 perfluoroalkyl, $R_2$ is H, $R_1$ and $R_2$ together are C4–C8 alkylene, or $R_1$ and $R_2$ together are bridged carbocyclic C4–C12 alkylene, when $X_2$ is C;

$R_1$ is H, C1–C8 alkyl, or C1–C4 perfluoroalkyl, and $R_2$ is omitted, when $X_2$ is N;

$R_7$ is H or methyl, $R_8$ is H or methyl, or $R_7$ and $R_8$ together are when $X_1$ is C;

$R_7$ is H or methyl, and $R_8$ is omitted, when $X_1$ is N; and $X_1$ may locate at another position of the hexagonal ring, when $X_1$ is N.

2. The Pt(II) complex as defined in item 1, wherein $X_1$ is C, and $R_7$ and $R_8$ together are 3. The Pt(II) complex as defined in Item 2, wherein $X_2$ is C.

4. The Pt(II) complex as defined in Item 3, wherein $R_1$ and $R_2$ together are bridged carbocyclic C4–C12 alkylene.

5. The Pt(II) complex as defined in Item 4, wherein $R_1$ and $R_2$ together are wherein $R_4$, $R_5$ and $R_6$ independently are C1–C4 alkyl.

6. The Pt(II) complex as defined in Item 5, wherein $R_4$, $R_5$, and $R_6$ are methyl.

7. The Pt(II) complex as defined in Item 3, wherein $R_1$ is C1—C8 alkyl, or C1–C4 perfluoroalkyl, and $R_2$ is hydrogen.

8. The Pt(II) complex as defined in Item 2, wherein $X_2$ is N, $R_1$ is C1–C8 alkyl, or C1–C4 perfluoroalkyl, and $R_2$ is omitted.
9. The Pt(II) complex as defined in Item 1, wherein $X_1$ is C, $R_7$ is H or methyl, and $R_8$ is H.
10. The Pt(II) complex as defined in Item 9, wherein $X_2$ is C.
11. The Pt(II) complex as defined in Item 10, wherein $R_1$ and $R_2$ together are bridged carbocyclic C4–C12 alkylene.
12. The Pt(II) complex as defined in Item 11, wherein $R_1$ and $R_2$ together are wherein $R_4$, $R_5$ and $R_6$ independently are C1–C4 alkyl.
13. The Pt(II) complex as defined in Item 12, wherein $R_4$, $R_5$ and $R_6$ are methyl.
14. The Pt(II) complex as defined in Item 10, wherein $R_1$ is C1–C8 alkyl, or C1–C4 perfluoroalkyl, and $R_2$ is hydrogen.
15. The Pt(II) complex as defined in Item 10, wherein $R_1$ and $R_2$ together are C4–C8 alkylene.
16. The Pt(II) complex as defined in Item 15, wherein $R_1$ and $R_2$ together are tetramethylene.
17. The Pt(II) complex as defined in Item 9, wherein $X_2$ is N, $R_1$ is C1–C8 alkyl, or C1–C4 perfluoroalkyl, and $R_2$ is omitted.
18. The Pt(II) complex as defined in Item 1, wherein $X_1$ is N, $R_7$ is H or methyl, and $R_8$ is omitted.
19. The Pt(II) complex as defined in Item 18, wherein $X_2$ is C.
20. The Pt(II) complex as defined in Item 19, wherein $R_1$ and $R_2$ together are bridged carbocyclic C4–C12 alkylene.
21. The Pt(II) complex as defined in Item 20, wherein $R_1$ and $R_2$ together are are wherein $R_4$, $R_5$ and $R_6$ independently are C1–C4 alkyl.
22. The Pt(II) complex as defined in Item 21, wherein $R_4$, $R_5$ and $R_6$ are methyl.
23. The Pt(II) complex as defined in Item 19, wherein $R_1$ is C1–C8 alkyl, or C1–C4 perfluoroalkyl, and $R_2$ is hydrogen.
24. The Pt(II) complex as defined in Item 19, wherein $R_1$ and $R_2$ together are C4–C8 alkylene.
25. The Pt(II) complex as defined in Item 24, wherein $R_1$ and $R_2$ together are tetramethylene.
26. The Pt(II) complex as defined in Item 18, wherein $X_2$ is N, $R_1$ is C1–C8 alkyl, or C1–C4 perfluoroalkyl, and $R_2$ is omitted.

DETAILED DESCRIPTION OF THE INVENTION

Figure 1:
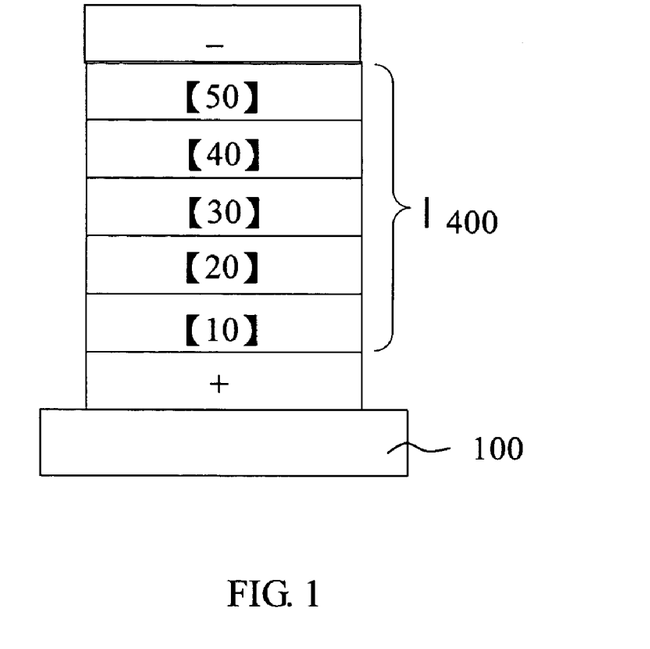
FIG. 1 shows a schematic diagram of a multi-layered OLED of the present invention.

In the following text, the synthesis and spectrum data of the phosphorescent Pt complexes according to the present invention are described in detail, as well as the application of this type of complexes as a phosphorescent material of an organic light-emitting diode (OLED). The configuration of an OLED can be in a two layered, three layered, or multiple layered structures. FIG. 1 is a schematic diagram of a multiple layered OLED device, wherein the actual thickness of each layer is independent of the dimension depicted in the drawing. The structure of the multiple layered OLED device, in sequence, comprises a substrate (100), an anode (+), a hole injection modification layer (10), a hole transporting layer (20), an electron-blocking layer (not shown in the drawing), a light emitting layer (30), a hole-blocking layer (40), an electron transporting layer (50), and a cathode (−). Said electron-blocking layer, hole injection modification layer (10), and hole-blocking layer (40), depending on the requirements of said device, may or may not be included in the structure thereof, wherein the layers between the positive electrode and the negative electrode constitute an electroluminescent medium (400) of said device. Said light emitting layer (30) is formed by doping a phosphorescence material as a dopant into a host compound.

General procedures: All reactions were performed under nitrogen. Solvents were distilled from appropriate drying agents prior to use. Commercially available reagents were used without further purification unless otherwise stated. All reactions were monitored by TLC with Merck pre-coated glass plates (0.20 mm with fluorescent indicator $UV_{254}$). Compounds were visualized with UV light irradiation at 254 nm and 365 nm. Flash column chromatography was carried out using silica gel from Merck (230–400 mesh). Mass spectra were obtained on a JEOL SX-102A instrument operating in electron impact (EI) or fast atom bombardment

(FAB) mode. $^1$H and $^{13}$C NMR spectra were recorded on a Bruker-400 or INOVA-500 instrument; chemical shifts are quoted with respect to the internal standard tetramethylsilane for $^1$H and $^{13}$C NMR data. Elemental analysis was carried out with a Heraeus CHN-O Rapid Elementary Analyzer.

Spectroscopic and Dynamic Measurements: Steady-state absorption and emission spectra were recorded on a Hitachi (U-3310) spectrophotometer and an Edinburgh (FS920) fluorimeter, respectively. Both wavelength-dependent excitation and emission response of the fluorimeter were calibrated. A configuration of front-face excitation was used to measure the emission of the solid sample, in which the cell was made by assembling two edge-polished quartz plates with various Teflon spacers. A combination of appropriate filters was used to avoid interference from the scattering light. Lifetime studies were performed by an Edinburgh FL 900 photon-counting system with a hydrogen-filled/or a nitrogen lamp as the excitation source. Data were analyzed using a nonlinear least squares procedure in combination with an iterative convolution method. The emission decays were analyzed by the sum of exponential functions, which allows partial removal of the instrument time broadening and consequently renders a temporal resolution of ~200 ps.

To determine the photoluminescence quantum yield in solution, samples were degassed by three freeze-pump-thaw cycles under vigorous stirring conditions. 4-(Dicyanomethylene)-2-methyl-6-(p-dimethylaminostyryl)-4H-pyran (DCM, $\lambda_{em}$=615 nm, Exciton, Inc.) in methanol was used as a reference, assuming a quantum yield of 0.43 with a 430 nm excitation. [J. M. Drake, M. L. Lesiecki, D. M. Camaioni, Chem. Phys. Lett. 1985, 113, 530.] An integrating sphere (Labsphere) was applied to measure the quantum yield in the solid state, in which the solid sample film was prepared via either spin coating or vapor deposition methods and was excited by a 514 nm (complex 1) or 457 nm (complex 2) Ar$^+$ laser line. The resulting luminescence was led to an intensified charge-coupled detector for subsequent quantum yield analyses. To obtain the PL quantum yield in solid state, the emission was collected via integrating sphere, and the quantum yield was calculated according to a reported method. [J. C. de Mello, H. F. Wittmann, R. H. Friend, Adv. Mater. 1997, 9, 230.]

OLED Fabrication. Charge transporting materials such as NPB {4,4'-bis[N-(1-naphthyl)-N-phenylamino]biphenyl} and Alq$_3$ [tris(8-hydroxyquinolinato)aluminium (III)], as well as the host material CBP (4,4'-N.N'-dicarbazolyl-1,1'-biphenyl) were synthesized according to literature procedures, [A. Y. Sonsale, S. Gopinathan, C. Gopinathan, Indian J. Chem. 1976, 14, 408; B. E. Koene, D. E. Loy, M. E. Thompson, Chem. Mater. 1998, 10, 2235.] and were sublimed twice through a temperature-gradient sublimation system before use. BCP (2,9-dimethyl-4,7-diphenyl-1,10-phenanthroline) was obtained from Aldrich. Patterned ITO-coated glass substrates (sheet resistance$\leq$30 $\Omega$/□) with an effective individual device area of 3.14 mm$^2$ were cleaned by sonication in a detergent solution, water and ethanol, respectively and then dried by a flow of nitrogen. The substrates were further treated with oxygen plasma for 3 min before loading into the vacuum chamber. Various organic layers were deposited sequentially at a rate of 0.1~0.3 nm/s under a pressure of 2×10$^{-5}$ Torr in an Ulvac Cryogenic deposition system. Phosphorescent dopants were co-evaporated with CBP via two independent sources. A thin layer of LiF (1 nm) and a thick layer of Al (150 nm) were followed as the cathode. The current-voltage-luminance of the devices was measured in ambient conditions with a Keithley 2400 Source meter and a Newport 1835C Optical meter equipped with 818ST silicon photodiode. The EL spectrum was obtained using a HITACHI F4500 spectrofluorimeter. The active area of the device was 3.14 mm$^2$ and that of the silicon photodiode was 100 mm$^2$. The device was placed close to the photodiode such that all the forward light goes to the photodiode. The external quantum efficiency was calculated according to the method described before. [S. R. Forrest, D. D. C. Bradley, M. E. Thompson, Adv. Mater. 2003, 15, 1043.] The luminous flux(lm) is defined by $P_v=K_m\int_\lambda P_{e,\lambda}V(\lambda)d\lambda$; where $K_m$ is the maximum luminous efficiency (683 lm/W), $P_{e,\lambda}$ is the spectral concentration of radiant flux, $V(\lambda)$ is the relative photopic luminous efficiency function [G. Wyszecki, W. S. Stiles, "Color Science: Concepts and Methods, Quantitative Data and Formulae" John Wiley & Sons, New York, 1982. p. 259.]; the luminance (cd/m$^2$) is defined by luminous flux/$\pi$a, where a is the device area; the luminous efficiency (cd/A) is defined by luminous flux/$\pi$I, where I is the current; power efficiency is defined as luminous flux/IV, where V is the applied voltage.

Synthesis. The multi-step reactions giving the first two Pt(II) emitting complexes are shown in Scheme 1.

(Scheme 1)

(i) NaH, THF
(ii) N₂H₄, EtOH,
(iii) K₂PtCl₄, 80° C., 16 h.

These Pt(II) complexes exhibit enhanced emission quantum yields, short phosphorescence radiative lifetimes in the range of several microseconds and, more importantly, a much lower tendency in forming aggregation than previously reported Pt(II) porphyrinato or β-diketonato complexes for electroluminescent applications. [R. C. Kwong, S. Sibley, T. Dubovoy, M. Baldo, S. R. Forrest, M. E. Thompson, Chem. Mater. 1999, 11, 3709; C.-M. Che, Y.-J. Hou, M. C. W. Chan, J. Guo, Y. Liu, Y. Wang, J. Mater Chem. 2003, 13, 1362.] Remarkable improvement of the device performances has been achieved at higher dopant concentrations or even in a pure emission layer, constituting for the first time a highly efficient Pt(II)-based OLED in the red.

Figure 2:
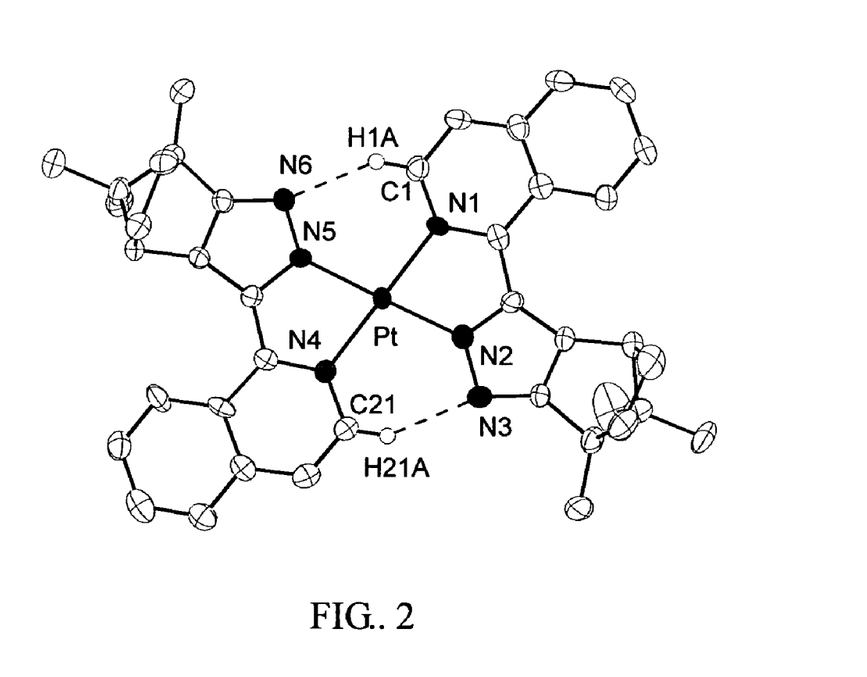
FIG. 2 shows the X-ray structure of a Pt complex 1 synthesized in Example 1 according to the present invention.

Characterization. Both Pt complexes, Pt(iqdz)₂ (1) and Pt(pydz)₂ (2), were highly soluble in organic solvents and have been characterized using various spectroscopic methods (see experimental section). Their spectroscopic data are in good agreement with the expected square planar Pt(II) complexes coordinated with two indazole chelates. Complex 1 was further examined by single crystal X-ray diffraction analysis to establish its molecular structure. FIG. 2 depicts the X-ray molecular structure of the complex 1.

Figure 3:
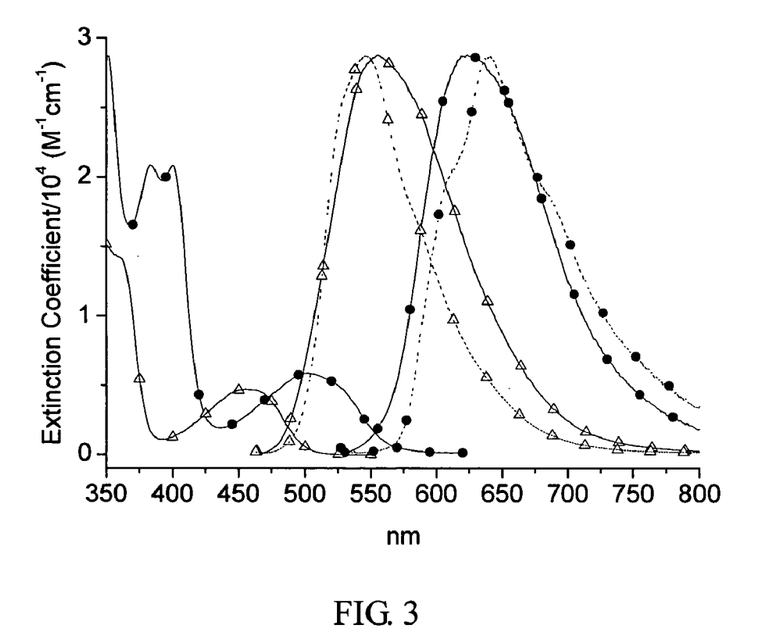
FIG. 3 shows the UV-Vis absorption and emission spectra of complex 1 ($2.68 \times 10^{-5}$ M, -●-) and complex 2 ($2.14 \times 10^{-5}$ M, -Δ-) in $CH_2Cl_2$ at room temperature. Note that the normalized emission spectra were acquired under degassed condition. The dot lines denote the corresponding solid-state emission obtained from a thin film sample at room temperature.
Figure 4A:
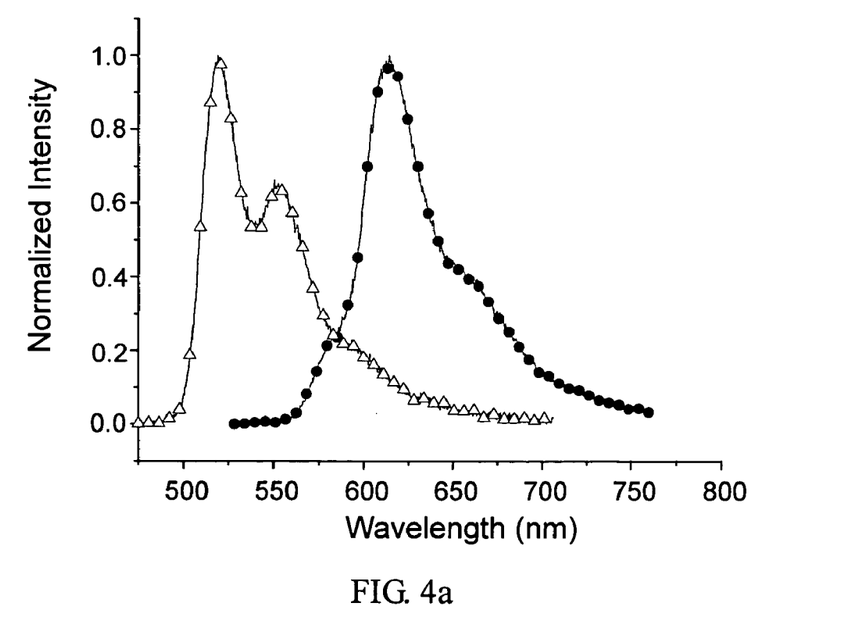
FIG. 4a shows the phosphorescence spectra of complex 1 (-●-) and complex 2 (-Δ-) in the 77 K solid $CH_2Cl_2$ matrices.
Figure 4B:
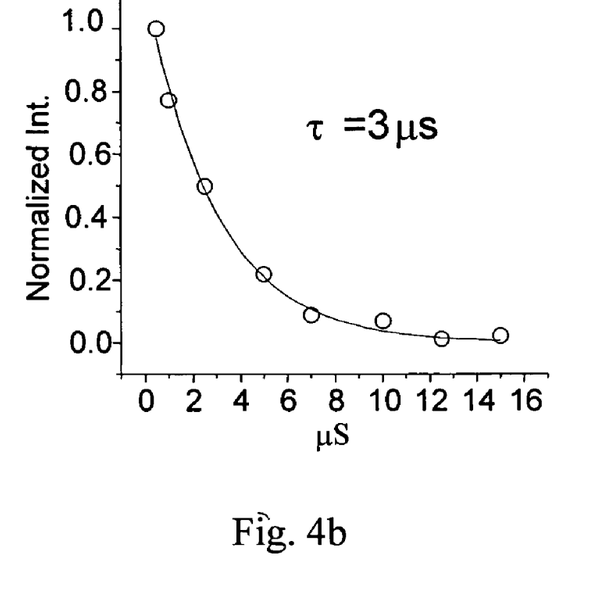
FIG. 4b shows the phosphorescence decay profiles of complex 1.
Figure 4C:
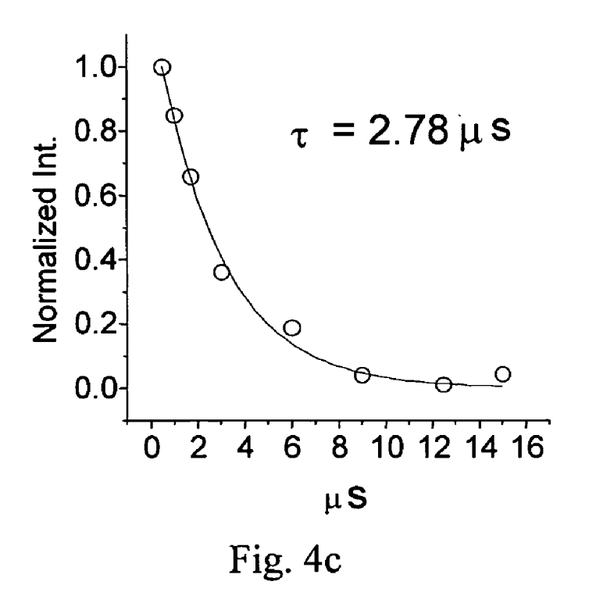
FIG. 4c shows the phosphorescence decay profiles of complex 2.

Photophysical Measurements. As shown in FIG. 3, although the energy gaps are quite different, similar spectral features are observed for complexes 1 and 2, consisting of a weak, broad band located in the long wavelength region, accompanied by a vibronic progression feature in the short wavelength region that is commonly assigned to the singlet π—π* intra-ligand transitions ($^1$IL). The low frequency absorption bands have a relatively small extinction coefficient (1: 5240 M⁻¹cm⁻¹ at 502 nm; 2: 4690 M⁻¹cm⁻¹ at 457 nm) are tentatively assigned to the transition incorporating a state mixing amongst singlet and triplet metal-ligand charge transfer ($^1$MLCT and $^3$MLCT) and, to a certain extent, the intra-ligand triplet state ($^3$IL). Support for this viewpoint is first provided by a distinct shoulder at 530 nm (ε~4080 M⁻¹ cm⁻¹) resolved in the absorption spectrum of complex 1, which can be tentatively assigned to the lowest lying $^3$MLCT band (vide infra). The close energetics and absorptivity between the $^1$MLCT and $^3$MLCT bands suggest that the $^3$MLCT transition, induced by spin-orbit coupling and the proximal energy levels with respect to $^1$MLCT, is greatly enhanced and becomes partially allowed. This novel spectral feature is in accord with data for other recently published Pt(II) complexes bearing bis(phenoxy)diimine auxiliaries capable of tetradentate bonding. [Y.-Y. Lin, S.-C. Chan, M. C. W. Chan, Y.-J. Hou, N. Zhu, C.-M. Che, Y. Liu, Y. Wang, Chem. Eur. J. 2003, 9, 1263.] Although the authors have not explicitly examined and discussed the details of the singlet-triplet mixing, its presence is unambiguously confirmed by the obvious overlap between this UV-Vis absorption band and the leading edge of the corresponding emission profile.

As for complex 2, the $^1$MLCT and $^3$MLCT states are so close that an asymmetric band was observed rather than the well-resolved dual absorption profile. Complex 1 exhibits an intensive emission maximized at 635 nm (Φ=0.81; τ=5.34 μs) in degassed CH₂Cl₂. The oxygen quenching rate of 1.78×10⁹ M⁻¹ s⁻¹ for the emission in CH₂Cl₂, in combination with its spectral mirror image with respect to the lowest absorption profile, leads us to conclude that the emission mainly originates from a triplet manifold. Similarly, complex 2 also exhibits strong phosphorescence with a peak wavelength at 553 nm (Φ=0.64; τ=3.63 μs), which is comparable to those observed in the cyclometalated dipyridyl-benzene Pt complexes. [J. A. G. Williams, A. Beeby, E. S. Davies, J. A. Weinstein, C. Wilson, Inorg. Chem. 2003, 42, 8609.] The observed radiative lifetimes for 1 and 2, respectively, in CH₂Cl₂ are relatively long for a pure $^3$MLCT emission from complexes incorporating a central heavy atom like Pt(II) and a $^1$MLCT state in proximity. Accordingly, we tentatively propose that there exists, in part, a further state mixing with the $^3$IL manifold. Firm support for this viewpoint is given by the unusually broad, structureless emission feature, with a full-width-at-half-maximum (fwhm) of 108 nm and 109 nm for 1 and 2, respectively in CH₂Cl₂ at RT, while upon cooling to 77 K the emission reveals distinctive vibronic-like features with peak wavelengths at 580, 614 (520), 656 (552) and 698 (596) nm for complex 1 and 2 (see FIG. 4 and Table 1), respectively. Although not well resolved, similar structural features were also observed for both complexes in the solid state at RT (see FIG. 3). The spectral progression of >1000 cm⁻¹ for each successive peak cannot be rationalized by the much smaller d level splitting in a square planar coordination, but is akin to that corresponding to the vibrational modes (1270~1300 cm⁻¹) of aromatic terpyridyl ligands. [Q.-Z. Yang, L.-Z. Wu, Z.-X. Wu, L.-P. Zhang, C.-H. Tung, Inorg. Chem. 2002, 41, 5653; V. W.-W. Yam, R. P.-L. Tang, K. M.-C. Wong, K.-K. Cheung, Organometallics 2001, 20, 4476.] Alternatively, it may be plausible that the broad fwhm, together with the vibronic structure features in a 77 K CH₂Cl₂ solution as well as in the solid state at RT, arises from a state mixing between $^3$MLCT and $^3$IL. [J. DePriest, G. Y. Zheng, N. Goswami, D. M. Eichhorn, C. Woods, D. P. Rillema, Inorg. Chem. 2000, 39, 1955; G. Y. Zheng, D. P. Rillema, J. DePriest, C. Woods, Inorg. Chem. 1998, 37, 3588; G. Y. Zheng, D. P. Rillema, Inorg. Chem. 1998, 37, 1392.] In a central planar configuration like 1 and 2, the strong mixing of these two transitions essentially requires covalent interaction of the relevant d orbitals and the ligand π system, in which MLCT [$d_{xz, yz} \to \pi^*$] transitions should be the most likely candidates. [W. B. Connick, V. M. Miskowski, V. H. Houlding, H. B. Gray, Inorg. Chem. 2000, 39, 2585.]

Due to the planar geometry of the central Pt(II) atom possessing a $dsp^2$ configuration, one has to consider the possible stacking effects for both 1 and 2. We thus carried out a concentration-dependent absorption/emission study in an attempt to resolve this issue. Upon varying the sample concentrations from $3.45\times10^{-5}$ M to $1.07\times10^3$ M, both absorption and emission spectra remain unchanged for 1 and 2, indicating that the stacking effect, if any, is too small to affect any associated photophysical behaviour. It is thus reasonable to conclude that the introduction of a bulky camphor derived group on the indazole fragment drastically increases the steric hindrance and hence suppresses aggregation. Supplementary support for this viewpoint is provided by the solid-state emission spectra in that both complexes (1: $\lambda_{em}$=638 nm; 2: $\lambda_{em}$=551 nm, see FIG. 3) manifest negligible spectral shifts from the corresponding emission maximum in solution, providing unambiguous evidence for the negligible stacking interaction in both complexes. It is noted that the solid film PL is narrower than the solution PL. In addition, the PL spectra in the solid film show slight blue shift for 2 and red shift for 1 in comparison with their corresponding emission in solution. If the solid state of a complex lacks strong intermolecular interaction such as hydrogen bonding, π stacking, etc., a slightly blue shift and narrowness for the solid film PL relative to that of the solution PL may be expected, and can be attributed to a "medium effect" For complex 2 in solution, the stronger interaction from the solvent (e.g. $CH_2C_2$) makes the emission broader, whereas due to the lack of π stacking, complex 2 is more or less frozen and inhibited from having a closer interaction with each other. In comparison, the additional fused benzene of isoquinoline in complex 1 introduces a weak but perhaps non-negligible π interaction in the solid film, resulting in a slightly red shifted emission. Nevertheless, from solution to solid, the shift of peak wavelength is rather small for 1, indicating that the intermolecular interaction cannot be large. This viewpoint can be supported from X-ray single crystal analysis, in which a rather long Pt . . . Pt distance has been resolved for 1 (vide supra).

Table 1 lists detailed spectroscopy and dynamics data for 1 and 2 in solution and in a single crystal. Despite the much lower energy gap with respect to that of the pyridyl counterpart 2, significant enhancement of the luminescent quantum yield (Φ~0.81) is observed in 1, accompanied by a longer lifetime (5.34 μs) in degassed $CH_2Cl_2$. These results seem to contradict the energy-gap law, in which the theory pertaining to radiationless decay concludes that the radiationless deactivation should increase upon decreasing the energy gap of the transition. [S. R. Johnson, T. D. Westmoreland, J. V. Caspar, K. R. Barqawi, T. J. Meyer, Inorg. Chem. 1988, 27, 3195; C. E. Whittle, J. A. Weinstein, M. W. George, K. S. Schanze, Inorg. Chem. 2001, 40, 4053.] We thus tentatively propose that the remarkable but unusual luminescence behaviour in complex 1 is due to the highly conjugated π systems in indazole coupled with the nearby isoquinoline fragments. One possible strategy to suppress the active vibrational modes, such as ring stretching and bending of the acceptor ligand that commonly dominates the deactivation of the MLCT excited states, is to use a ligand with a rigid σ-framework. In addition, upon excitation, the electron occupation of the lowest π* acceptor orbital results in increases of the C—C and C—N bond distances, inducing radiationless transition due to the loose bonding effect. [J. V. Caspar, T. D. Westmoreland, G, H. Allen, P. G. Bradley, T. J. Meyer, W. H. Woodruff, J. Am. Chem. Soc. 1984, 106, 3492; E. M. Kober, T. J. Meyer, Inorg. Chem. 1985, 24, 106.] Since the Franck-Condon factors for nonradiative transitions is qualitatively proportional to the square of the bonding displacement, enlarging the π conjugation should reduce the distortion of the ligand framework due to the smaller changes in average distance between ground and excited states. [A. El-Ghayoury, A. Harriman, A. Khatyr, R. Ziessel, Angew. Chem., Int. Ed. 2000, 39, 185; P. A. Anderson, F. R. Keene, T. J. Meyer, J. A. Moss, G. F. Strouse, J. A. Treadway, J. Chem. Soc. Dalton Trans. 2002, 3820; Y.-Q. Fang, N. J. Taylor, G. S. Hanan, F. Loiseau, R. Passalacqua, S. Campagna, H. Nierengarten, A. Van Dorsselaer, J. Am. Chem. Soc. 2002, 124, 7912.] Accordingly, the radiationless decay rate in 1 is expected to be relatively small to compete with the red phosphorescence, giving rise to an exceptionally high emission quantum yield. For comparison, Nazeeruddin and co-workers have recently reported near unity quantum yields for the blue, green and yellow emission by meticulous selection of the ligand on the Ir(III) system possessing strong ligand field strength, which increased the energy gaps between triplet emitting states and the nearby deactivating MC level. [M. K. Nazeeruddin, R. Humphry-Baker, D. Berner, S. Rivier, L. Zuppiroli, M. Graetzel, J. Am. Chem. Soc. 2003, 125, 8790.] Other factors leading to the high emission yield for 1 or 2 are also possible. These include (a) Pt(II) metal ion intrinsically possessing a relatively larger d-orbital splitting, (b) isoquniolinyl indazole (or pyridyl indazole) with a fairly strong ligand field inducing a larger gap between the MC states and the LUMO of the ligands and (c) close lying π—π* and MLCT states together with the heavy atom effect enhancing the spin-orbital coupling. A comprehensive understanding of the relaxation mechanisms might have to rely on future theoretical approaches, focus of which is currently in progress.

Figure 5:
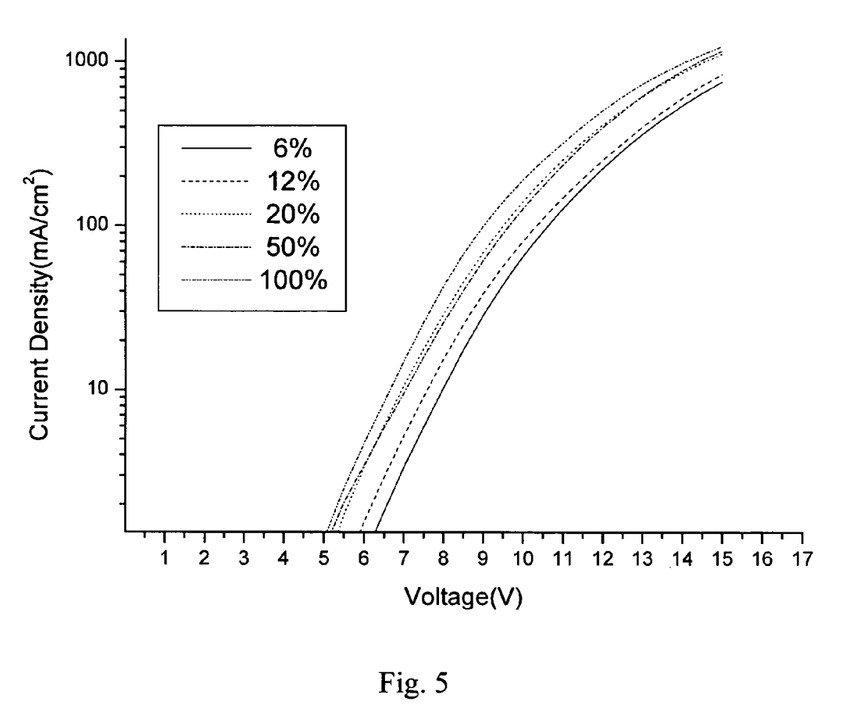
FIG. 5 shows I–V characteristics of complex 1-based OLED devices as a function of the dopant concentration.
Figure 6:
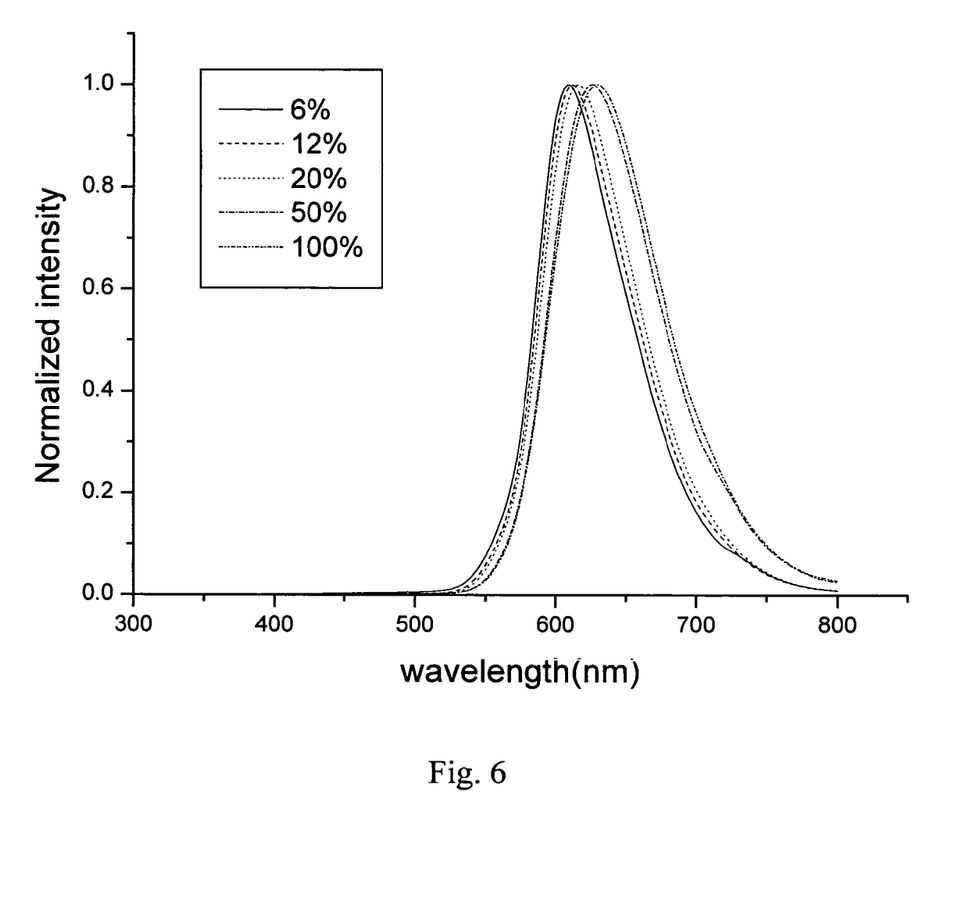
FIG. 6 shows electroluminescence spectra of complex 1-based OLED devices as a function of dopant concentrations.

OLED Fabrication. Due to its high phosphorescence quantum efficiency in the red, multilayer devices of the configuration ITO/NPB(40 nm)/CBP:1(30 nm)/BCP(10 nm)/Alq$_3$(30 nm)/LiF(1 nm)/Al(150 nm) were prepared, with doping concentrations of 1 varying from 6%, 12%, 20%, 50% to a neat film. Very bright red emission was observed for all the concentrations prepared, including the one with a pure layer of the platinum complex. The I–V curves, plotted in FIG. 5, show a trend of increasing current density with increasing concentrations of 1. The results may imply that the phosphorescent sites serve as charge trapping sites. The EL spectra originated solely from the complex in all cases, but with a small red shift of the EL spectra $\lambda_{max}$ upon increasing the dopant concentrations, being 610 and 630 nm for the 6% dopant concentration and the neat film, respectively (FIG. 6). The fwhm of the EL spectrum also increased slightly (from 76 nm to 92 nm) over the same range of doping concentrations. Comparing FIGS. 3 and 6, the EL from the device is slightly blue shifted from PL of the solid film. One possible origin for the shift is from the microcavity effect, which is caused by the interference between the forwarding light and the light reflected from the metal electrode. [A. Dodabalapur, L. J. Rothberg, T. M. Miller, E. W. Kwock, Appl. Phys. Lett. 1994, 64, 2486; S. K. So, W. K. Choi, L. M. Leung, K. Neyts, Appl. Phys. Lett. 1999, 74, 1939; Y. Fukuda, T. Watanabe, T. Wakimoto, S. Miyaguchi, M. Tsuchida, Synth. Met. 2000, 111–112, 1.]

Figure 7:
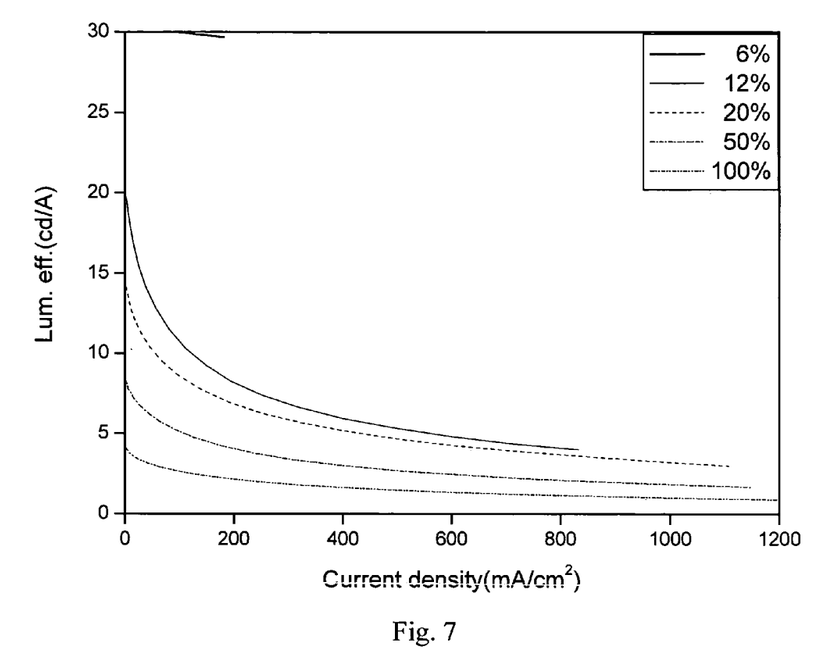
FIG. 7 shows luminance efficiencies of complex 1-based OLED devices as a function of current density.

All devices showed a turn-on voltage of as low as 4.0 V. Although the devices exhibited a similar dropping trend with increasing current (FIG. 7), as is the case for most phosphorescence-based devices, the performance characteristics are nevertheless very encouraging. For the device doped with 12% of 1 driven at a current of 100 mA, a brightness of 10677 cd/m$^2$ was achieved with an external quantum efficiency of ~7%, a luminance efficiency of ~11 cd/A and a power efficiency of 3.3 lm/W. The results also exhibited a decreasing trend with increasing concentration of the platinum dopant. However, it is noteworthy that even using a pure film of 1 as the emission layer, a brightness of 2653 cd/m$^2$ and an external quantum efficiency of 2.46%, luminance efficiency of 2.65 cd/A and power efficiency of 0.93 lm/W can be achieved. The relatively high efficiency of the device even in the neat complex is tentatively attributed to the unusually short radiative lifetime that avoids the triplet—triplet annihilation. Table 2 summarizes the performance data for various concentrations studied. The achievement of high luminescence efficiency can be attributed to a much shorter phosphorescence radiative lifetime in combination with a rationally designed structure that greatly suppresses the aggregation effect. It should be noted that rigid steric blockers such as a pinene functionality incorporated into an octahedral phenyl pyridine Ir(III) complex have been reported to effectively reduce self-quenching of the phosphorescent dopant. [H. Z. Xie, M. W. Liu, 0. Y. Wang, X. H. Zhang, C. S. Lee, L. S. Hung, S. T. Lee, P. F. Teng, H. L. Kwong, H. Zheng, C. M. Che, Adv. Mater. 2001, 13, 1245.] While improving the device luminescence efficiency, this prior innovation based on Ir(ppy)$_3$ and its pinene derivatized complexes exhibits green emission rather than the much needed, saturated red emission.

Moreover, the phosphorescent OLEDs with configuration ITO/NPB(40 nm)/CBP:Pt(II) (30 nm)/BCP(10 nm)/Alq$_3$(30 nm)/LiF(1 nm)/Al(150 nm) are also prepared using the green emitting Pt(II) complexes 2 and 5, respectively. Their device performance characteristics are summarized in Tables 3 and 4. As indicated from the data, bright green emission was observed for all the concentrations prepared, showing max. brightness of ~73000 cd/m$^2$ with the highest external quantum efficiency ($\eta_{ext}$)~6.6%, which are comparable to the best performing cyclometalated complex Ir(ppy)$_3$.

TABLE 1

Photophysical properties of selected Pt(II) complexes in degassed CH$_2$Cl$_2$ at RT (298 K).

| | $\lambda_{abs}^{max}$ ($\epsilon$, M$^{-1}$cm$^{-1}$) | PL $\lambda_{max}$ [nm] | $\Phi$ | $\tau$ [$\mu$s] |
|---|---|---|---|---|
| Pt(iqdz)$_2$ (1) | 502, (5240) | 635 | 0.81 | 5.34 |
| | | (610, 638, 688)[a] | 0.20[a] | 1.10[a,c] |
| | | (580, 614, 656, 698)[b] | | 3.0[b] |
| Pt(pydz)$_2$ (2) | 457, (4690) | 553 | 0.64 | 3.63 |
| | | (528, 550, 581)[a] | 0.15[a] | 3.38[a,c] |
| | | (520, 552, 596)[b] | | 2.78[b] |
| Pt(iq3dz)$_2$ (3) | 450, (1996) | 587 | 0.24 | 1.65 |
| Pt(bqpz)$_2$ (8) | 466, (5286) | 584, 631 | 0.74 | 13.0 |

[a]The solid-state emission obtained from a thin film sample at RT.
[b]The phosphorescent emission recorded in frozen CH$_2$Cl$_2$ matrices at 77 K.
[c]Lifetime is an average value from a two-component fit.

TABLE 2

Performance characteristics for the OLED devices based on complex 1.

| Doping conc. | Brightness (cd/m$^2$) | $\eta_{ext}$ (%) | Lum. Eff. (Cd/A) | Power Eff. (lm/W) | $V_{drive}$ (V) | $V_{turn-on}$ (V) | FWHM (nm) | CIE (x, y) |
|---|---|---|---|---|---|---|---|---|
| 6% | 3451[a] | 10.6 | 17.43 | 6.37 | 8.61 | 4 | 610/76 | 0.61, 0.38 |
| | 10846[b] | 6.6 | 10.92 | 3.24 | 10.61 | | | |
| | 33193(15)[c] | 14.9(5.5) | 24.57(5.5) | 14.86(5.0) | | | | |
| 12% | 3210[a] | 10.51 | 16.21 | 6.20 | 8.24 | 3.8 | 612/78 | 0.62, 0.37 |
| | 10677[b] | 6.98 | 10.76 | 3.28 | 10.32 | | | |
| | 33394(15)[c] | 12.8(6.0) | 19.79(6.0) | 12.43(4.5) | | | | |
| 20% | 2378[a] | 8.28 | 11.97 | 4.95 | 7.6 | 3.5 | 616/80 | 0.63, 0.37 |
| | 8592[b] | 5.95 | 8.59 | 2.84 | 9.5 | | | |
| | 33454(15)[c] | 10.2(5.0) | 14.7(5.0) | 9.28(4.5) | | | | |
| 50% | 1397[a] | 6.23 | 7.04 | 2.87 | 7.71 | 3.6 | 626/88 | 0.64, 0.36 |
| | 5101[b] | 4.55 | 5.14 | 1.68 | 9.63 | | | |
| | 19430(15)[c] | 8.00(4.5) | 9.03(4.5) | 6.31(4.5) | | | | |
| 100% | 694[a] | 3.24 | 3.5 | 1.52 | 7.23 | 3.8 | 630/92 | 0.64, 0.35 |
| | 2653[b] | 2.46 | 2.65 | 0.93 | 9.01 | | | |
| | 10733(15)[c] | 3.91(4.5) | 4.22(4.5) | 2.95(4.5) | | | | |

[a]values collected under 20 mA/cm$^2$
[b]values collected under 100 mA/cm$^2$
[c]max values of the devices; values in the parentheses are the voltages at which they were obtained.

TABLE 3

Performance characteristics for the OLED devices based on complex 2.

| Doping conc. | Brightness (cd/m$^2$) | $\eta_{ext}$ (%) | Lum. Eff. (Cd/A) | Power Eff. (lm/W) | $V_{drive}$ (V) | $V_{turn-on}$ (V) | FWHM (nm) | CIE (x, y) |
|---|---|---|---|---|---|---|---|---|
| 6% | 4657[a] | 6.59 | 23.34 | 9.89 | 7.42 | 3.6 | 542/78 | 0.35, 0.56 |
| | 17453[b] | 4.95 | 17.54 | 5.88 | 9.39 | | | |
| | 59807(15)[c] | 7.10(6.5) | 25.13(6.5) | 13.58(5.0) | | | | |

TABLE 3-continued

Performance characteristics for the OLED devices based on complex 2.

| Doping conc. | Brightness (cd/m$^2$) | $\eta_{ext}$ (%) | Lum. Eff. (Cd/A) | Power Eff. (lm/W) | $V_{drive}$ (V) | $V_{turn-on}$ (V) | FWHM (nm) | CIE (x, y) |
|---|---|---|---|---|---|---|---|---|
| 50% | 3890[a] | 5.53 | 19.60 | 12.56 | 4.92 | 2.7 | 556/82 | 0.41, 0.55 |
|  | 14481[b] | 4.12 | 14.60 | 7.22 | 6.37 |  |  |  |
|  | 53663(15)[c] | 6.54(3.5) | 23.17(3.5) | 20.83(3.5) |  |  |  |  |
| 100% | 4110[a] | 6.14 | 20.65 | 14.29 | 4.55 | 2.6 | 568/82 | 0.45, 0.52 |
|  | 16152[b] | 4.84 | 16.25 | 8.36 | 6.12 |  |  |  |
|  | 54628(15)[c] | 6.52(3.5) | 21.9(3.5) | 19.68(3.5) |  |  |  |  |

[a]values collected under 20 mA/cm$^2$
[b]values collected under 100 mA/cm$^2$
[c]max values of the devices; values in the parentheses are the voltages at which they were obtained.

TABLE 4

Performance characteristics for the OLED devices based on complex 5.

| Doping conc. | Brightness (cd/m$^2$) | $\eta_{ext}$ (%) | Lum. Eff. (Cd/A) | Power Eff. (lm/W) | $V_{drive}$ (V) | $V_{turn-on}$ (V) | FWHM (nm) | CIE (x, y) |
|---|---|---|---|---|---|---|---|---|
| 6% | 2357[a] | 4.19 | 11.82 | 5.47 | 6.80 | 4.0 | 502/60 | 0.19, 0.50 |
|  | 9937[b] | 3.54 | 9.99 | 3.75 | 8.39 |  |  |  |
|  | 44656(15)[c] | 4.23(6.5) | 11.95(6.5) | 6.37(5.5) |  |  |  |  |
| 50% | 1484[a] | 2.19 | 7.40 | 4.33 | 5.39 | 3.1 | 520/74 | 0.28, 0.58 |
|  | 7141[b] | 2.12 | 7.16 | 3.34 | 6.74 |  |  |  |
|  | 38960(15)[c] | 2.20(5.5) | 7.44(5.5) | 4.82(4.0) |  |  |  |  |
| 100% | 4602[a] | 6.54 | 23.02 | 16.10 | 4.49 | 2.8 | 542/96 | 0.37, 0.57 |
|  | 19402[b] | 5.57 | 19.60 | 10.81 | 5.72 |  |  |  |
|  | 73342(15)[c] | 6.64(4.0) | 23.38(4.0) | 18.37(4.0) |  |  |  |  |

[a]values collected under 20 mA/cm$^2$
[b]values collected under 100 mA/cm$^2$
[c]max values of the devices; values in the parentheses are the voltages at which they were obtained.

EXPERIMENTS

Example 1

Synthesis of 4,8,8-Trimethyl-3-isoquinoline-1-yl-4,5,6,7-tetrahydro-2H-4,7-methano-indazole, (iqdz)H To a stirred mixture of NaH (0.26 g, 10.8 mmol) and THF (10 mL) at 0° C. was added a solution of (1R)-(+)-camphor (1.64 g, 10.8 mmol) in THF for a period of 10 min. The temperature of the reaction mixture was slowly increased to RT and stirring was continued for about 30 min. Then the solution was heated to 60° C., and ethyl 1-isoquinolinecarboxylate (1.7 g, 8.5 mmol) in THF was added slowly and refluxed for about 3 h. After this period, the reaction mixture was cooled to 0° C. and quenched with dilute HCl until pH=8–9. Then it was extracted with ethyl acetate (2×100 mL), and the extracts were washed with brine, and water, dried over anhydrous MgSO$_4$ and concentrated in vacuo to give a yellow oil (2.2 g). Without further purification, to a refluxing solution of the above oil (2.2 g) in EtOH (30 mL) was added dropwise hydrazine monohydrate (4.2 mL, 86.0 mmol) in EtOH. After the mixture was refluxed for 12 h, the solvent was removed under vacuum. The residue obtained was dissolved in ethyl acetate and washed with water, dried over anhydrous MgSO$_4$ and concentrated again. The residue obtained was passed through a silica gel column using mixtures of hexane and ethyl acetate as eluents to give (iqdz)H as colorless crystals (1.4 g, 55%).

Spectral data: MS (EI), m/z 303, M$^+$. $^1$H NMR (500 MHz, CDCl$_3$, 294 K): δ 8.51 (d, J=5.8 Hz, 1H), 8.42 (d, J=8.3 Hz, 1H), 7.81 (d, J=8.4 Hz, 1H), 7.67 (ddd, J=8.3, 6.8, 1.3 Hz, 1H), 7.61 (ddd, J=8.4, 6.8, 1.5 Hz, 1H), 7.56 (d, J=5.8 Hz, 1H), 3.00 (d, J=4.0 Hz, 1H), 2.19 (m, 1H), 1.92 (m, 1H), 1.44 (m, 2H), 1.35 (s, 3H), 0.98 (s, 3H), 0.79 (s, 3H). $^{13}$C NMR (125 MHz, CDCl$_3$, 294 K): δ 167.1, 149.9, 141.8, 136.8, 132.5, 130.2, 127.3, 127.0, 126.3, 126.2, 125.5, 120.1, 61.0, 50.4, 50.0, 33.6, 27.5, 20.5, 19.2, 10.6. Anal. Calcd. for C$_{20}$H$_{21}$N$_3$: C, 79.17; H, 6.98; N, 13.85. Found: C, 79.49; H, 6.98; N, 13.92.

Synthesis of Pt(iqdz)$_2$ (1)

A solution of potassium tetrachloroplatinate (K$_2$PtCl$_4$) (0.1 g, 0.24 mmol), (iqdz)H (0.16 g, 0.53 mmol) in a mixture of ethanol (15 mL) and water (5 mL) was heated at 80° C. for about 16 h. After this period, the reaction mixture was cooled and the precipitated solid was filtered off, washed with ether and dried under vacuum to give Pt(iqdz)$_2$ as a red solid (1, 0.15 g, 78%). Crystals of 1 suitable for X-ray analysis were obtained by recrystallization from a mixture of dichloromethane and hexane at room temperature.

Spectra data of 1: MS (FAB), m/z 800, M$^+$. $^1$H NMR (400 MHz, CD$_2$Cl$_2$, 294 K): δ 10.93 (d, J=6.4 Hz, 2H), 8.86 (d, J=8.2 Hz, 2H), 7.94 (d, J=7.8 Hz, 2H), 7.86 (dd, J=8.2, 7.0 Hz, 2H), 7.76 (dd, J=7.8, 7.0 Hz, 2H), 7.63 (d, J=6.4 Hz, 2H), 3.44 (d, J=2.8 Hz, 2H), 2.34 (m, 2H), 2.02 (m, 2H), 1.58~1.47 (m, 4H), 1.52 (s, 6H), 1.09 (s, 6H), 0.85 (s, 6H). $^{13}$C NMR (100 MHz, CD$_2$Cl$_2$, 294 K): δ 164.8, 156.5, 144.2, 142.1, 136.9, 132.1, 128.2, 127.8, 127.6, 126.9, 123.8, 118.4, 60.8, 52.8, 50.7, 34.1, 27.9, 20.5, 19.4; 10.9 Anal. Calcd for C$_{40}$H$_{40}$N$_6$Pt; C, 60.43; H, 5.32; N, 10.31. Found: C, 60.52; H, 5.29; N, 10.58.

Example 2

Synthesis of 4,8,8-Trimethyl-3-pyridin-2-yl-4,5,6,7-tetrahydro-2H-4,7-methano-indazole, (pydz)H Using the same conditions as for (iqdz)H, starting from ethyl picolinate and (1R)-(+)-camphor, the title compound was obtained as white crystals (yield 34%).

Spectral data: MS (EI), m/z 253, M$^+$. $^1$H NMR (500 MHz, CDCl$_3$, 294 K): δ 8.58 (d, J=5.5 Hz, 1H), 7.69 (ddd, J=7.8, 7.5, 1.8), 7.53 (d, J=7.8 Hz, 1H), 7.15 (ddd, J=7.5, 5.5, 1.3 Hz, 1H), 3.03 (d, J=4.5 Hz, 1H), 2.14 (m, 1H), 1.87 (m, 1H), 1.35 (m, 1H), 1.24 (m, 1H) 1.31 (s, 3H), 0.98 (s, 3H), 0.71 (s, 3H). $^{13}$C NMR (125 MHz, CDCl$_3$, 294 K): δ 167.6, 149.2, 149.1, 136.9, 133.5, 124.6, 122.1, 120.5, 61.2, 50.3, 48.2, 33.5, 27.2, 20.5, 19.3, 10.5. Anal. Calcd. for C$_{16}$H$_{19}$N$_3$: C, 75.85; H, 7.56; N, 16.59. Found: C, 76.07; H, 7.48; N, 16.60.

Synthesis of Pt(pydz)$_2$ (2)

Using the same conditions as for Pt(iqdz)$_2$ (1), starting from K$_2$PtCl$_4$ and the ligand (pydz)H, the title compound 2 was obtained as a yellow powder (yield 50%).

Spectral data of 2: MS (FAB), m/z 700, M$^+$. $^1$H NMR (500 MHz, CDCl$_3$, 294 K): δ 10.72 (brs, 2H), 7.82 (dd, J=7.5, 7.5 Hz, 2H), 7.52 (d, J=8.0 Hz, 2H), 7.22 (brs, 2H), 3.03 (d, J=4.0 Hz, 2H), 2.13 (m, 2H), 1.86 (m, 2H), 1.35–1.44 (m, 2H), 1.19 (m, 2H), 1.42 (s, 6H), 97 (s, 6H), 0.78 (s, 6H). $^{13}$C NMR (125 MHz, CDCl$_3$, 294 K): δ 164.5, 155.0, 152.8, 142.5, 138.7, 126.1, 120.9, 118.2, 61.8, 50.9, 47.9, 33.8, 27.8, 20.8, 19.7, 11.2. Anal. Calcd. for C$_{32}$H$_{36}$N$_6$Pt: C, 54.93; H, 5.19; N, 12.01. Found: C, 54.85; H, 5.22; N, 11.91.

Selected crystal data of 1: C$_{40}$H$_{40}$N$_6$Pt, M=799.87, monoclinic, space group P 2$_1$/n, a=6.8567(3), b=18.4625(9), c=15.5327(8) Å, β=95.824(1)°, V=1956.6(16) Å$^3$, Z=2, ρ$_{calcd}$=1.358 mgm$^{-3}$, F(000)=800, crystal size=0.40×0.10×0.03 mm, λ(Mo—K$_α$)=0.7107 Å, T=295(2) K, μ=3.620 mm$^{-1}$, 18030 reflections collected (R$_{int}$=0.0467), final R$_1$[I>2σ(I)]=0.0573 and wR$_2$(all data) =0.1552.

Example 3

Synthesis of Pt(iq3dz)$_2$ (3)

A solution of potassium tetrachloroplatinate (K$_2$PtCl$_4$) (0.1 g, 0.24 mmol), 3-isoquinoline-3-yl-7,8,8-trimethyl-4,5,6,7-tetrahydro-2H-4,7-methano-indazole, (iq3dzH, 0.16 g, 0.53 mmol) in a mixture of ethanol (15 mL) and water (5 mL) was heated at 80° C. for about 16 h. After cooling the mixture to room temperature, the precipitate was collected, washed with diethyl ether and dried under vacuum to give yellow solid 52% (0.1 g, 0.13 mmol). Crystals of Pt(iq3dz)$_2$ suitable for X-ray analysis were obtained by recrystallization from a mixture of dichloromethane and hexane at room temperature.

Spectra data of (3): MS (FAB), observed m/z (actual) [assignment]: 800 (800) [M$^+$]. $^1$H NMR (400 MHz, CDCl$_3$, 294 K): δ 11.78 (s, 2H), 8.16 (d, J=8.0 Hz, 2H), 7.81–7.73 (m, 6H), 7.55 (ddd, J=6.8, 6.6,1.3 Hz, 2H), 3.17 (d, J=4.0 Hz, 2H), 2.20 (m, 2H), 1.92 (m, 2H), 1.50 (m, 6H), 1.46(2H, m),1.29 (m, 2H), 1.03 (s, 6H), 0.85 (s, 6H). $^{13}$C NMR (125 MHz, CDCl$_3$, 294 K): δ 168.9 (2C), 157.3 (2C), 148.3 (2C), 142.2 (2C), 136.7 (2C), 132.9 (2C), 129.7 (2C),126.9 (2C), 126.4 (2C), 126.1 (2C), 124.2 (2C), 113.4 (2C), 61.7 (2C), 50.7 (2C), 48.0 (2C), 34.0 (2C), 27.9 (2C), 20.9 (2C), 19.8 (2C), 11.2 (2C). Anal. Calcd. for C$_{40}$H$_{40}$N$_6$Pt: C, 60.43; H, 5.32; N, 10.31. Found: C, 60.52; H, 5.29; N, 10.58.

Figure 8:
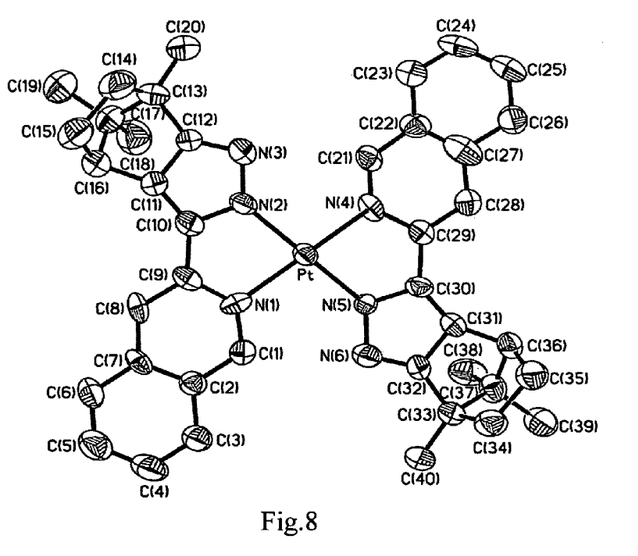
FIG. 8 shows the X-ray structure of a Pt complex 3 synthesized in Example 3 according to the present invention.

Selected crystal data of (3): C$_{40}$H$_{40}$N$_6$Pt, M=799.87, orthorhombic, space group P 2$_1$/n, a=7.0868(3), b=16.9811 (8), c=30.3358(15) Å, β=90.00 (1)°, V=3650.7(3) Å$^3$, Z=4, ρ$_{calcd}$=1.455 mgm$^{-3}$, F(000)=1600, crystal size=0.25×0.12×0.05 mm, λ(Mo—K$_α$)=0.7107 Å, T=295(2) K, μ=3.879 mm$^{-1}$, 43030 reflections collected (R$_{int}$=0.0452), final R$_1$[I>2σ(I)]=0.0553 and wR$_2$(all data) =0.1280. FIG. 8 depicts the X-ray molecular structure of the complex 3.

Example 4

Synthesis of Pt(mppz)₂ (4)

To the suspension of NaH (15 mg, 0.63 mmol) in 15 mL of THF was added 3-methyl-5-(2-pyridyl) pyrazole (mppzH, 83 mg, 0.52 mmol) slowly at room temperature. After being stirred for 1.5 hour, the solution was filtered and transferred into a reaction flask loaded with 100 mg of Pt(DMSO)$_2$Cl$_2$ (0.24 mmol) and 10 mL of THF. The solution was refluxed for 12 hours. After then, the solvent was evaporated under vacuum and 60 mL of CH$_2$Cl$_2$ was added to extract the product. The extract was then washed with water, dried with anhydrous Na$_2$SO$_4$, giving a yellowish green material after removal of all solvent. Further purification was conducted using vacuum sublimation (160° C., 220 mtorr), affording 80 mg of Pt(mppz)$_2$ as bright green solid (0.16 mmol, 65%).

Spectra data of (4): MS (EI, 70 eV), observed m/z (actual) [assignment]: 511 (511) [M⁺]. ¹H NMR (500 MHz, CDCl$_3$, 294 K): δ 10.64 (d, $^3J_{HH}$=6.0 Hz, 2H), 7.86 (t, $^3J_{HH}$=8.0 Hz, $^3J_{HH}$=8.0 Hz, 2H), 7.55 (d, $^3J_{HH}$=8.0 Hz, 2H), 7.28 (t, $^3J_{HH}$=6.0 Hz, $^3J_{HH}$=6.0 Hz, 2H), 6.43 (s, 2H), 2.45 (s, 6H). ¹³C NMR (125 MHz, CDCl$_3$, 294K): δ 154.7 ($C_{py}$), 152.5 ($C_{pz}$), 150.3 ($CH_{py}$), 147.6 ($C_{pz}$), 139.1 ($CH_{py}$), 121.6 ($CH_{py}$), 118.2 ($CH_{py}$), 103.0 ($CH_{pz}$), 14.0 ($CH_3$). Anal. Calcd. for C$_{18}$H$_{16}$N$_6$Pt: C, 42.27; N, 16.43; H, 3.15. Found: C, 42.08; N, 16.38; H, 3.49.

Example 5

Synthesis of Pt(bppz)₂ (5)

To the suspension of NaH (14 mg, 0.58 mmol) in 15 mL of THF was added 3-tert-butyl-5-(2-pyridyl) pyrazole (bppzH, 110 mg, 0.54 mmol) slowly at room temperature. After being stirred for 1.5 hour, the solution was filtered and transferred into a flask that loaded with 100 mg of Pt(DMSO)$_2$Cl$_2$ (0.24 mmol) and 10 mL of THF. The solution was refluxed for 12 hours. After then, the solvent was evaporated and 60 mL of CH$_2$Cl$_2$ was added to extract the product. The extract was then washed with water, dried with anhydrous Na$_2$SO$_4$, giving a green material after removal of all solvent. Further purification was conducted using vacuum sublimation (160° C., 220 mtorr) and recrystallization from CH$_2$Cl$_2$ and hexane gave 76 mg of Pt(bppz)$_2$ as bright green solid (0.13 mmol, 54%).

Spectra data of (5): MS (EI, 70 eV), observed m/z (actual) [assignment]: 595 (595) [M⁺]. ¹H NMR (400 MHz, CDCl$_3$, 294 K): δ10.79 (d, $^3J_{HH}$=6.0 Hz, 2H), 7.82 (ddd, $^3J_{HH}$=7.9 Hz, $^3J_{HH}$=7.6 Hz, $^4J_{HH}$=1.2 Hz, 2H), 7.55 (d, $^3J_{HH}$=7.9 Hz, 2H), 7.19 (ddd, $^3J_{HH}$=7.6 Hz, $^3J_{HH}$=6.0 Hz, $^4J_{HH}$=1.2 Hz, 2H), 6.49 (s, 2H), 1.42 (s, 18H). ¹³C NMR (125 MHz, CDCl$_3$, 294K): δ 161.4 ($C_{py}$), 155.4 ($C_{pz}$), 152.3 ($CH_{py}$), 149.4 ($C_{pz}$), 138.8 ($CH_{py}$), 120.7 ($CH_{py}$), 117.8 ($CH_{py}$), 99.4 ($CH_{pz}$), 32.6 ($C_{t-butyl}$), 31.0 ($CH_3$). Anal. Calcd. for C$_{24}$H$_{28}$N$_6$Pt: C, 48.40; N, 14.11; H, 4.74. Found: C, 48.31; N, 14.10; H, 4.88.

Example 6

Synthesis of Pt(fppz)₂ (6)

To the suspension of NaH (17 mg, 0.71 mmol) in 15 mL of THF was added 3-trifluoromethyl-5-(2-pyridyl) pyrazole (fppzH, 120 mg, 0.56 mmol) slowly at room temperature. After being stirred for 1 hour, the solution was filtered and transferred into a flask that loaded with 100 mg of Pt(DMSO)$_2$Cl$_2$ (0.24 mmol) and 10 mL of THF. The solution was refluxed for 8 hours. Purification was conducted using sublimation (150° C., 200 mtorr) and recrystallization from CHCl$_3$, giving 83 Mg of Pt(fppz)$_2$ as orange fine needles (0.13 mmol, 56%).

Spectra data of (6): MS (EI, 70 eV), observed m/z (actual) [assignment]: 619 (619) [M⁺], 407 (407) [M⁺-fppz]. ¹H NMR (400 MHz, d-acetone, 294 K): δ 10.29 (d, $^3J_{HH}$=6.0 Hz, 2H), 8.19 (ddd, $^3J_{HH}$=7.6 Hz, $^3J_{HH}$=7.6 Hz, $^4J_{HH}$=1.4 Hz, 2H), 7.94 (d, $^3J_{HH}$=7.6 Hz, 2H), 7.47 (ddd, $^3J_{HH}$=7.6 Hz, $^3J_{HH}$=6.0 Hz, $^4J_{HH}$=1.4 Hz, 2H), 7.067 (s, 2H). ¹⁹F (470 MHz, d-toluene, 294 K): δ –60.70l (s, CF$_3$). Anal. Calcd. for C$_{18}$H$_{10}$F$_6$N$_6$Pt: C, 34.90; N, 13.57; H, 1.63. Found: C, 34.44; N, 13.12; H, 1.78.

Example 7

Synthesis of Pt(hppz)$_2$ (7)

To the suspension of NaH (13 mg, 0.54 mmol) in 15 mL of THF was added 3-heptafluoropropyl-5-(2-pyridyl) pyrazole (hppzH, 150 mg, 0.48 mmol) slowly at room temperature. After being stirred for 1 hour, the solution was filtered and transferred into a reaction flask loaded with 100 mg of Pt(DMSO)$_2$Cl$_2$ (0.24 mmol) and 10 mL of THF. The solution was refluxed for 12 hours and the solvent was completely removed under vacuum. The solid residue was sublimed under vacuum (110° C., 200 mtorr). Further recrystallization from CH$_2$Cl$_2$ at room temperature gave 113 mg of Pt(hppz)$_2$ as yellow needles (0.14 mmol, 58%).

Spectra data of (7): MS (EI, 70 eV), observed m/z (actual) [assignment]: 820 (819) [M$^+$]. $^1$H NMR (500 MHz, d-THF, 294 K): δ 10.53 (d, $^3J_{HH}$=6.0 Hz, 2H), 8.14 (ddd, $^3J_{HH}$=7.5 Hz, $^3J_{HH}$=7.5 Hz, $^4J_{HH}$=1.0 Hz, 2H), 7.95 (d, $^3J_{HH}$=7.5 Hz, 2H), 7.48 (ddd, $^3J_{HH}$=7.5 Hz, $^3J_{HH}$=6.0 Hz, $^4J_{HH}$=1.0 Hz, 2H), 7.13 (s, 2H). $^{19}$F (470 MHz, d-THF, 294 K): δ−80.83 (t, $^3J_{FF}$=8.5 Hz, CF$_3$), −109.06 (dd, $^3J_{FF}$=19.3 Hz, $^3J_{FF}$=8.5 Hz, CF$_2$), −127.31 (s, CF$_2$). Anal. Calcd. for C$_{22}$H$_{10}$F$_{14}$N$_6$Pt: C, 32.25; N, 10.26; H, 1.23. Found: C, 32.06; N, 10.08; H, 1.41.

Example 8

Synthesis of Pt(bqpz)$_2$ (8)

A solution of potassium tetrachloroplatinate (K$_2$PtCl$_4$) (100 mg, 0.24 mmol), 1-(5-tert-butyl-2H-pyrazol-3-yl)-isoquinoline (bqpzH, 130 mg, 0.52 mmol) in a mixture of ethanol (15 mL) and water (5 mL) was heated at 80° C. for about 16 h. After cooling the mixture to room temperature the precipitated solid was collected, washed with diethyl ether and dried under vacuum to give Pt(bqpz)$_2$ as orange solid (85 mg, 0.122 mmol) in 51% yield.

Spectra data of (8): MS (FAB), observed m/z (actual) [assignment] 696 (696) [M$^+$]. $^1$H NMR (400 MHz, CD$_2$Cl$_2$, 294 K): δ 10.98 (d, J=5.6 Hz, 2H), 8.82 (d, J=7.9 Hz, 2H), 7.95 (d, J=7.9 Hz, 2H), 7.86 (t, J=7.0 Hz, 2H), 7.77 (t, J=7.4 Hz, 2H), 7.66 (d, J=5.7 Hz, 2H), 7.06 (s, 2H), 1.55(s, 18H). Anal. Calcd. for C$_{32}$H$_{32}$N$_6$Pt: C, 55.24; H, 4.64; N, 12.08. Found: C, 54.88; H, 4.94; N, 11.98.

Example 9

Synthesis of Pt(bzpz)$_2$ (9)

To the suspension of NaH (13 mg, 0.54 mmol) in 20 mL of THF was added 3-tert-butyl-5-(2-pyrazine) pyrazole (bzpzH, 100 mg, 0.5 mmol) slowly at room temperature. After being stirred for 1.5 hour, the solution was filtered and transferred into a reaction flask loaded with 100 mg of Pt(DMSO)$_2$Cl$_2$ (0.24 mmol) and 10 mL of THF. The solution was refluxed for 12 hours and the solvent was removed under vacuum. The solid residue was sublimed under vacuum (180° C., 160 mtorr). Further recrystallization from CH$_2$Cl$_2$ at room temperature gave 98 mg of Pt(bzpz)$_2$ as red fine needles (0.16 mmol, 68%).

Spectra data of (9): MS (EI, 70 eV), observed m/z (actual) [assignment]: 597 (597) [M$^+$], 582 (582) [M-CH$_3$]. $^1$H NMR (500 MHz, CDCl$_3$, 294 K): δ 10.54 (d, $^3J_{HH}$=3.8 Hz, 2H), 8.83 (s, 2H), 8.38 (d, $^3J_{HH}$=3.8 Hz, 2H), 6.50 (s, 2H), 1.43 (s, 18H). $^{13}$C NMR (125 MHz, CDCl$_3$, 294 K): δ 162.4 (C$_{py}$), 149.7 (C$_{pz}$), 145.9 (C$_{pz}$), 144.2 (CH$_{py}$), 141.9 (CH$_{py}$), 140.6 (CH$_{py}$), 100.9 (CH$_{pz}$), 32.7 (C$_{t\text{-}butyl}$), 30.9 (CH$_3$). Anal. Calcd. for C$_{22}$H$_{26}$N$_8$Pt: C, 44.22; N, 18.75; H, 4.39. Found: C, 43.94; N, 19.21; H, 4.60.

Example 10

Synthesis of Pt(bmpz)$_2$ (10)

To the suspension of NaH (8 mg, 0.33 mmol) in 15 mL of THF was added 3-tert-butyl-5-(5-methyl-2-pyrazine) pyrazole (bmpzH, 60 mg, 0.28 mmol) slowly at room temperature. After being stirred for 1.5 hour, the solution was filtered and transferred into a reaction flask loaded with 50 mg of Pt(DMSO)$_2$Cl$_2$ (0.12 mmol) and 10 mL of THF. The solution was refluxed for 10 hours and the solvent was removed under vacuum. The solid residue was sublimed under vacuum (180° C., 200 mtorr). Further recrystallization from a mixture of CH$_2$Cl$_2$ and hexane gave 48 mg of Pt(bmpz)$_2$ as orange crystals (0.08 mmol, 65%).

Spectra data of (10): MS (EI, 70 eV), observed m/z (actual) [assignment]: 626 (625) [M$^+$], 611 (610) [M$^+$-CH$_3$]. $^1$H NMR (500 MHz, CDCl$_3$, 294 K): δ 10.65 (s, 2H), 8.80 (s, 2H), 6.55 (s, 2H), 2.71 (s, 6H) 1.43 (s, 18H). $^{13}$C NMR (125 MHz, CDCl$_3$, 294 K): δ 162.1 (C$_{py}$), 151.9 (C$_{pz}$), 146.9 (C$_{pz}$), 146.5 (CH$_{py}$), 143.9 (CH$_{py}$), 139.5 (CH$_{py}$), 99.9 (C$_{pz}$), 32.7 (C$_{t\text{-}butyl}$), 30.9 (CH$_3$), 21.6 (CH$_3$). Anal. Calcd. for C$_{24}$H$_{30}$N$_8$Pt: C, 46.07; N, 17.91; H, 4.83. Found: C, 46.15; N, 17.70; H, 5.02.

Example 11

Synthesis of Pt(bptz)$_2$ (11)

To the suspension of NaH (16 mg, 0.67 mmol) in 20 mL of THF was added 2-(5-tert-butyl-2H-[1,2,4]triazol-3-yl)-pyridine (bptzH, 110 mg, 0.5 mmol) slowly at room temperature. After being stirred for 1.5 hour, the solution was filtered and transferred into a reaction flask loaded with 100 mg of Pt(DMSO)$_2$Cl$_2$ (0.24 mmol) and 10 mL of THF. The solution was refluxed for 10 hours and the solvent was removed. The solid residue was sublimed under vacuum (160° C., 300 mtorr). Further recrystallization from a mixture of CH$_2$Cl$_2$ and pentane gave 90 mg of Pt(bptz)$_2$ as red orange crystals (0.15 mmol, 63%).

Spectra data of (11): MS (EI, 70 eV), observed m/z (actual) [assignment]: 597 (597) [M$^+$]. $^1$H NMR (400 MHz, CDCl$_3$, 294 K): δ 10.49 (d, 3J$_{HH}$=6.0 Hz, 2H), 8.07(d, $^3$J$_{HH}$=7.6 Hz, 2H), 8.00 (ddd, $^3$J$_{HH}$=7.6 Hz, $^3$J$_{HH}$=7.6 Hz, $^4$J$_{HH}$=1.2 Hz, 2H), 7.40 (ddd, $^3$J$_{HH}$=7.6 Hz, $^3$J$_{HH}$=6.0 Hz, $^4$J$_{HH}$=1.2 Hz, 2H), 1.49 (s, 18H). Anal. Calcd. for C$_{22}$H$_{26}$N$_8$Pt: C, 44.22; N, 18.75; H, 4.39. Found: C, 44.12; N, 18.69; H, 4.48.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A Pt(II) complex having the following formula:

wherein

X$_1$ and X$_2$ independently are C or N;

R$_1$ is H, C1–C8 alky, or C1–C4 perfluoroalkyl, R$_2$ is H, or R$_1$ and R$_2$ together are C4–C8 alkylene, or R$_1$ and R$_2$ together are bridged carbocyclic C4–C12 alkylene, when X$_2$ is C;

R$^1$ is H, C1–C8 alkyl, or C1–C4 perfluoroalkyl, and R$_2$ is omitted, when X$_2$ is N;

R$_7$ is H or methyl, R$_8$ is H or methyl, or R$_7$ and R$_8$ together are when X$_1$ is C;

R$_7$ is H or methyl, and R$_8$ is omitted, when X$_1$ is N.

2. The Pt(II) complex as defined in claim 1, wherein X$_1$ is C, and R$_7$ and R$_8$ together are 3. The Pt(II) complex as defined in claim 2, wherein X$_2$ is C.

4. The Pt(II) complex as defined in claim 3, wherein R$_1$ and R$_2$ together are bridged carbocyclic C4–C12 alkylene.

5. The Pt(II) complex as defined in claim 4, wherein R$_1$ and R$_2$ together are wherein R$_4$, R$_5$ and R$_6$ independently are C1–C4 alkyl.

6. The Pt(II) complex as defined in claim 5, wherein R$_4$, R$_5$ and R$_6$ are methyl.

7. The Pt(II) complex as defined in claim 3, wherein R$_1$ is C1–C8 alkyl, or C1–C4 perfluoroalkyl, and R$_2$ is hydrogen.

8. The Pt(II) complex as defined in claim 2, wherein $X_2$ is N, $R_1$ is C1–C8 alkyl, or C1–C4 perfluoroalkyl, and $R_2$ is omitted.

9. The Pt(II) complex as defined in claim 1, wherein $X_1$ is C, $R_7$ is H or methyl, and $R_8$ is H.

10. The Pt(II) complex as defined in claim 9, wherein $X_2$ is C.

11. The Pt(II) complex as defined in claim 10, wherein $R_1$ and $R_2$ together are bridged carbocyclic C4–C12 alkylene.

12. The Pt(II) complex as defined in claim 11, wherein $R_1$ and $R_2$ together are are wherein $R_4$, $R_5$ and $R_6$ independently are C1–C4 alkyl.

13. The Pt(II) complex as defined in claim 12, wherein $R_4$, $R_5$ and $R_6$ are methyl.

14. The Pt(II) complex as defined in claim 10, wherein $R_1$ is C1–C8 alkyl, or C1–C4 perfluoroalkyl, and $R_2$ is hydrogen.

15. The Pt(II) complex as defined in claim 10, wherein $R_1$ and $R_2$ together are C4–C8 alkylene.

16. The Pt(II) complex as defined in claim 10, wherein $R_1$ and $R_2$ together are tetramethylene.

17. The Pt(II) complex as defined in claim 9, wherein $X_2$ is N, $R_1$ is C1–C8 alkyl, or C1–C4 perfluoroalkyl, and $R_2$ is omitted.

18. The Pt(II) complex as defined in claim 1, wherein $X_1$ is N, $R_7$ is H or methyl, and $R_8$ is omitted.

19. The Pt(II) complex as defined in claim 18, wherein $X_2$ is C.

20. The Pt(II) complex as defined in claim 19, wherein $R_1$ and $R_2$ together are bridged carbocyclic C4–C12 alkylene.

21. The Pt(II) complex as defined in claim 20, wherein $R_1$ and $R_2$ together are are wherein $R_4$, $R_5$ and $R_6$ independently are C1–C4 alkyl.

22. The Pt(II) complex as defined in claim 21, wherein $R_4$, $R_5$ and $R_6$ are methyl.

23. The Pt(II) complex as defined in claim 19, wherein $R_1$ is C1–C8 alkyl, or C1–C4 perfluoroalkyl, and $R_2$ is hydrogen.

24. The Pt(II) complex as defined in claim 19, wherein $R_1$ and $R_2$ together are C4–C8 alkylene.

25. The Pt(II) complex as defined in claim 24, wherein $R_1$ and $R_2$ together are tetramethylene.

26. The Pt(II) complex as defined in claim 18, wherein $X_2$ is N, $R_1$ is C1–C8 alkyl, or C1–C4 perfluoroalkyl, and $R_2$ is omitted.

* * * * *